(12) United States Patent
Bianco

(10) Patent No.: US 7,399,933 B2
(45) Date of Patent: Jul. 15, 2008

(54) BREAST MEASUREMENT DEVICE AND METHOD FOR USE IN BREAST REDUCTION SURGERY

(76) Inventor: Angela Mary Margaret Bianco, 1319 Laperriere Ave, Ottawa, Ontario (CA) K12 7R9

( * ) Notice: Subject to any disclaimer, the term of this patent is extended or adjusted under 35 U.S.C. 154(b) by 401 days.

(21) Appl. No.: 11/210,654

(22) Filed: Aug. 25, 2005

(65) Prior Publication Data
US 2007/0054596 A1 Mar. 8, 2007

(30) Foreign Application Priority Data
Sep. 3, 2004 (CA) .................................. 2478966

(51) Int. Cl.
*A61B 5/103* (2006.01)
*G01G 19/00* (2006.01)
(52) U.S. Cl. ....................... 177/150; 600/587; 128/845; 177/200
(58) Field of Classification Search ................. 600/587; 128/845; 177/150, 199, 200
See application file for complete search history.

(56) References Cited

U.S. PATENT DOCUMENTS

| | | | | |
|---|---|---|---|---|
| 701,684 A | * | 6/1902 | Cowey | .................. 177/37 |
| 3,270,558 A | * | 9/1966 | Barret et al. | .................. 73/172 |
| 4,259,585 A | * | 3/1981 | Novak et al. | .................. 378/37 |
| 5,485,855 A | * | 1/1996 | Shiraiwa et al. | ............. 600/587 |
| 5,830,159 A | * | 11/1998 | Netta | .......................... 600/587 |
| 6,565,519 B2 | * | 5/2003 | Benesh | ....................... 600/587 |

* cited by examiner

*Primary Examiner*—Randy W Gibson

(57) ABSTRACT

A pre-operative breast measurement device and method for use in breast reduction surgery. The breast measurement device comprises a base portion and a support post mounted thereon, the support post being height adjustable so as to accommodate differing body heights of users. First and second breast measurement scales, which are width adjustable, are positioned on the support post, the scales being substantially perpendicular in relation to the support post, whereby the first breast measurement scale measures a weight of a first breast and the second breast measurement scale measures a weight of a second breast. A support saddle on the support post receives and supports a chin of a user during the measuring of the first breast and the second breast. The breast measurements provided by the scale thus provide a surgeon with an exact result of how much breast tissue must be removed from each breast during surgery so as to achieve a substantially symmetrical balance between the breasts after the surgery is completed.

8 Claims, 5 Drawing Sheets

BREAST MEASUREMENT DEVICE AND METHOD FOR USE IN BREAST REDUCTION SURGERY

The present invention relates to a breast measurement device and method for using the device in breast reduction surgery, and, more particularly, to a pre-operative breast measurement device and method for use in breast reduction surgery which will assist the surgeon in achieving a substantially symmetrical balance in a final size and shape between the breasts after the surgery is completed.

DESCRIPTION OF THE PRIOR ART

Bi-lateral mammaplasty, which can also referred to as breast reduction surgery, has become fairly common in recent years. Many medical practitioners regularly perform bi-lateral mammaplasty procedures and a number of surgical procedures are considered standard to accomplish a breast reduction. As an example, in Aesthetic Plastic Surgery, Rees, Saunders Company, 1980, Volume II, Chapter 33, a number of well known bi-lateral mammaplasty procedures are described. Among the relevant procedures are the Aries-Pitanguy and McKissock techniques and in each, a lateral wedge technique is typically required which is difficult to master. Consequently, consistent good symmetrical results, particularly with large breasts or with breasts which are of differing sizes before surgery, are difficult to achieve.

U.S. Pat. No. 4,892,096 (Nurayanan et al) describes a breast marking device for use in reconstructive breast surgery which provides a non-permanent mark which is concentric to the areola of a breast, and which can assist the surgeon in providing an aesthetically satisfactory appearance of a reconstructed breast. However, a problem still exists in that current surgical techniques and devices for use during breast reduction surgeries, including those referred to above, do not ensure that each of the patient's breasts will be proportionate after the reduction mammaplasty is performed. It can be said that current techniques for breast reduction surgery regularly require some guesswork by the physician and is an inexact science, in that the final shape and size of the breast is often determined by the surgeon's sense of proportion and the patient's pre-existing build. For example, while a surgeon may repeatedly remove breast tissue from the second of the two breasts and measure same until it equals that of the breast tissue removed from the first breast, this still does not ensure that the breasts will be proportionate and symmetrical after surgery.

Accordingly, there is a need for a breast measurement device and method which can be used in breast reduction surgery to accurately measure and weigh each breast before surgery, thus providing a surgeon with a valuable tool in calculating an exact result which must be removed from each breast during surgery so as to achieve a substantially symmetrical balance in a final size and shape between the breasts after the surgery is completed.

SUMMARY OF THE INVENTION

The present invention seeks to overcome the problems associated with performing a breast reduction surgery on a patient by providing an improved breast reduction device and method for using same. It is thus an object of the present invention to provide an improved breast reduction device and method of using same to provide a surgeon with a means to accurately measure and weigh each breast before breast reduction surgery.

It is another object of the present invention to provide an improved breast reduction device and method of using same which allows a surgeon with a means to calculate an exact result, from the measurements of the breasts, of how much breast tissue must be removed from each breast during surgery so as to achieve a substantially symmetrical balance in a final size and shape between the breasts after the surgery is completed.

According to one aspect of the present invention, there is provided a breast reduction apparatus for use in breast reduction surgery to reduce the size of at least one breast, said apparatus comprising a base portion; an upstanding support post mounted on the base portion; at least one breast measurement scale attached to the support post, the at least one breast measurement scale being substantially perpendicular in relation to the support post; and a support saddle for receiving and supporting a chin of a user, the support saddle being mounted upon an upper portion of the support post.

According to another aspect of the present invention, there is provided a breast reduction apparatus for pre-operative use in breast reduction surgery to reduce the size of at least one breast, said apparatus comprising a base portion; an upstanding support post mounted on the base portion; at least one breast measurement scale attached to an upper portion of the support post for measuring a weight of the at least one breast, the at least one breast measurement scale being substantially perpendicular in relation to the support post; and a support saddle for receiving and supporting a chin of a user during the measuring of the at least one breast, the support saddle being mounted upon the support post.

According to a still further aspect of the present invention, there is provided a breast reduction apparatus for pre-operative use in breast reduction surgery, said apparatus comprising a base portion;

an upstanding support post mounted on the base portion, the upstanding support post being height adjustable so as to accommodate differing body heights of users; first and second breast measurement scales, each of the scales being positioned at a substantially upper location on the support post and each being positioned on opposite sides of the support post from one another, the scales being substantially perpendicular in relation to the support post, whereby the first breast measurement scale measures a weight of a first breast and the second breast measurement scale measures a weight of a second breast; and a support saddle for receiving and supporting a chin of a user during the measuring of the first breast and the second breast, the support saddle being mounted upon the support post.

According to yet another aspect of the present invention, there is provided a breast reduction apparatus for pre-operative use in breast reduction surgery, said apparatus comprising a base portion;

an upstanding support post mounted on the base portion, the upstanding support post being height adjustable so as to accommodate differing body heights of users; a first and second support platform, the first and second support platform being positioned at a substantially upper location on the support post and each being positioned on opposite sides of the support post from one another, wherein the first and second support platform are substantially perpendicular in relation to the support post and horizontally adjustable so as to accommodate differing body widths of users; first and second breast measurement scales, the first breast measurement scale being mounted upon the first support platform and the second breast measurement scale being mounted upon the second support platform, whereby the first breast measurement scale measures a weight of a first breast and the second breast measurement scale measures a weight of a second breast so as to enable a surgeon to determine a quantity of breast tissue which must be removed during the breast reduction surgery from each of the first breast and the second breast so as to substantially provide a symmetric balance in a size and shape between the first breast and the second breast after the surgery is completed; and a support saddle for receiving and supporting a chin of a user during the measuring of the first breast and the second breast, the support saddle being mounted upon the support post.

According to yet another aspect of the present invention, there is provided a use of the breast reduction apparatus as defined in the present invention for pre-operative use in breast reduction surgery, whereby the weight of the first breast and the weight of the second breast is measured so as to enable a surgeon to determine a quantity of breast tissue which must be removed during the breast reduction surgery from each of the first breast and the second breast so as to substantially provide a symmetric balance in a size and shape between the first breast and the second breast after the surgery is completed.

According to a still further aspect of the present invention, there is provided a breast reduction method for pre-operative use in breast reduction surgery which utilizes the breast reduction apparatus as defined in the present invention comprising utilizing the first breast measurement scale to measure a weight of a first breast; utilizing the second breast measurement scale to measure a weight of a second breast; determining, based upon the measurements of the weight of the first and the second breast, a quantity of breast tissue which must be removed during the breast reduction surgery from each of the first breast and the second breast so as to substantially provide a symmetric balance in a size and shape between the first breast and the second breast after the surgery is completed; and removing the determined quantity of breast tissue from each of the first breast and the second breast.

According to a still further aspect of the present invention, there is provided a breast reduction system for pre-operative use in breast reduction surgery comprising a breast measurement apparatus having a base portion, an upstanding support post mounted on the base portion, a first and second support platform, the first and second support platform being positioned at a substantially upper location on the support post and each being positioned on opposite sides of the support post from one another, wherein the first and second support platform are substantially perpendicular in relation to the support post, first and second breast measurement scales, the first breast measurement scale being mounted upon the first support platform and the second breast measurement scale being mounted upon the second support platform, whereby the first breast measurement scale measures a weight of a first breast and the second breast measurement scale measures a weight of a second breast so as to enable a surgeon to determine a quantity of breast tissue which must be removed during the breast reduction surgery from each of the first breast and the second breast so as to substantially provide a symmetric balance in a size and shape between the first breast and the second breast after the surgery is completed, and a support saddle for receiving and supporting a chin of a user during the measuring of the first breast and the second breast, the support saddle being mounted upon the support post; utilizing the first breast measurement scale to measure a weight of a first breast; utilizing the second breast measurement scale to measure a weight of a second breast; determining, based upon the measurements of the weight of the first and the second breast, a quantity of breast tissue which must be removed during the breast reduction surgery from each of the first breast and the second breast so as to substantially provide a symmetric balance in a size and shape between the first breast and the second breast after the surgery is completed; and removing the determined quantity of breast tissue from each of the first breast and the second breast.

According to a still further aspect of the present invention, there is provided a breast reduction apparatus for pre-operative use in breast reduction surgery, said apparatus comprising a base portion; an upstanding support post mounted on the base portion, the upstanding support post being height adjustable so as to accommodate differing body heights of users; at least one breast measurement scale being positioned at a substantially upper location on the support post, wherein the at least one breast measurement scale is substantially perpendicular in relation to the support post and horizontally adjustable so as to accommodate differing body widths of users; and at least one support saddle, the at least one support saddle being mounted upon the at least one breast measurement scale, whereby the at least one breast measurement scale measures a weight of a breast placed thereon so as to enable a surgeon to determine a quantity of breast tissue which must be removed during the breast reduction surgery from the breast.

The advantage of the present invention is that it provides a simple and effective device which can assist surgeons in accurately assessing weight and size differences between breasts before breast reduction surgery, thus helping to reduce the subjectiveness of the surgeons sense of proportion during surgery in ensuring that each of the patient's breasts will be proportionate after the reduction surgery is performed A further advantage of the present invention is that it provides an improved breast reduction device and method of using same which allows a surgeon with a means to calculate an exact result, from the measurements of the breasts, of how much breast tissue must be removed from each breast during surgery so as to achieve a substantially symmetrical balance in a final size and shape between the breasts after the surgery is completed.

BRIEF DESCRIPTION OF THE DRAWINGS

A preferred embodiment of the present invention is described below with reference to the accompanying drawings, in which.

DESCRIPTION OF THE PREFERRED EMBODIMENT

Figure 1:
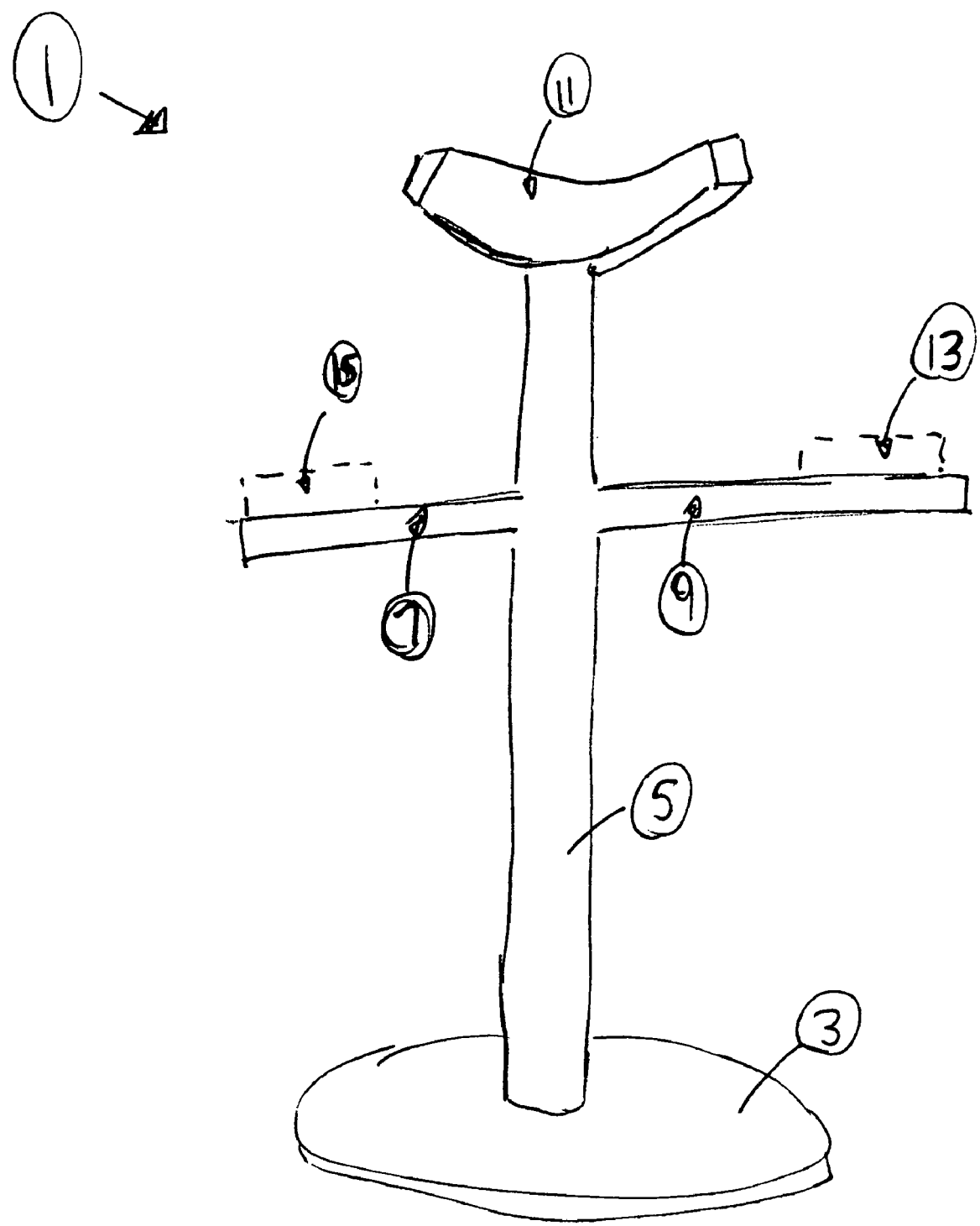
FIG. 1 illustrates an embodiment of the breast reduction device of the present invention.
Figure 2:
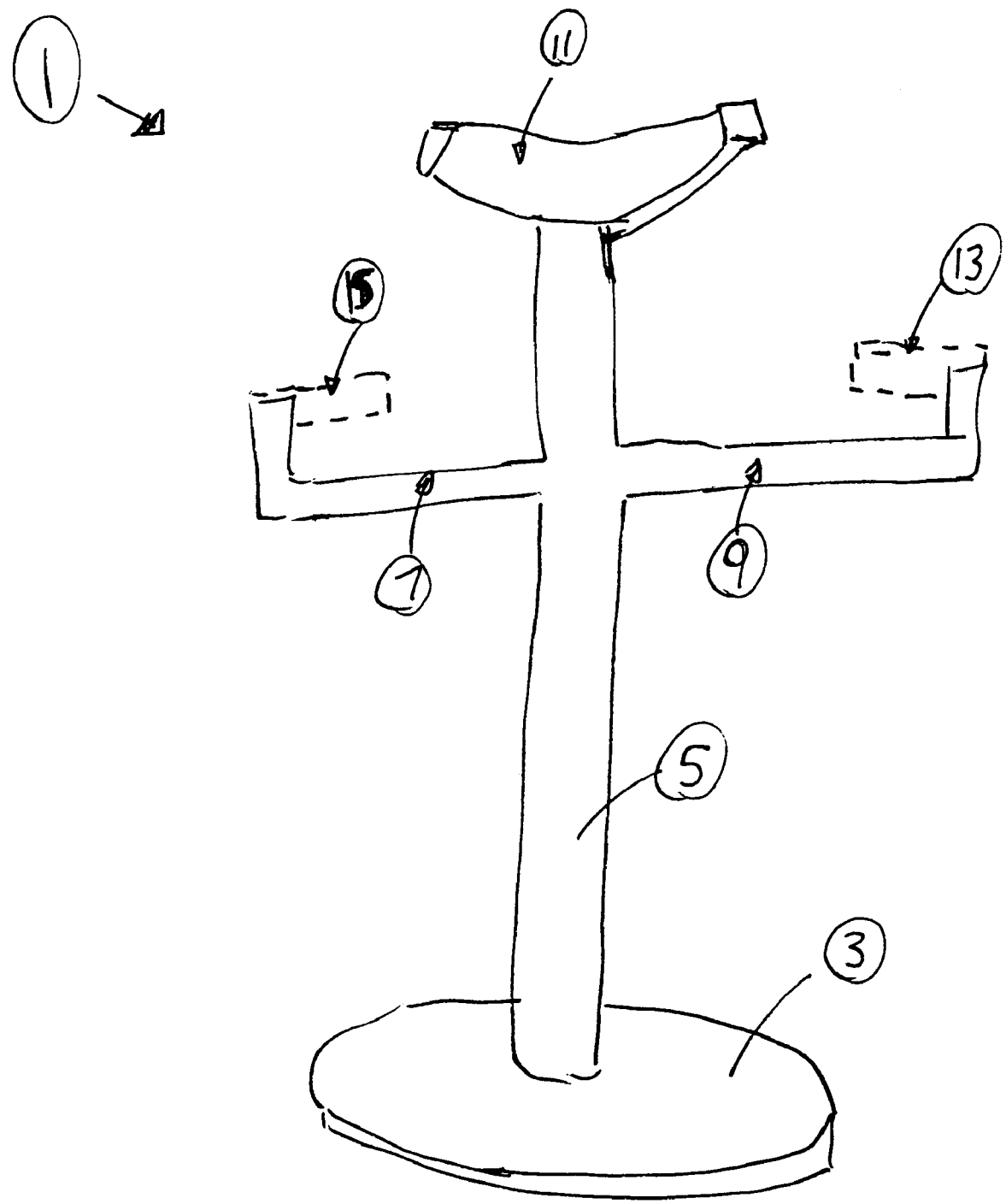
FIG. 2 illustrates another embodiment of the breast reduction device of the present invention.

In the preferred embodiment and as shown in FIGS. 1 and 2, the breast reduction device 1 of the present invention comprises a base portion 3 and an upstanding support post 5 mounted on the base portion 3. In one embodiment, the upstanding support post 5 can be height adjustable so as to accommodate differing body heights of users. Typically, this can be accomplished through the use of telescoping members (not shown) or other configurations which would be apparent to workers skilled in the art. In an embodiment of the present invention, the support post 5 can be rotatably mounted with respect to the base portion 3 about a vertical axis. In a still further embodiment of the present invention, the support post 5 can be rigidly mounted upon the base portion 3.

A first 7 and second support platform 9 are connected to the support post, the first 7 and second support platform 9 being positioned at a substantially upper location on the support post 5 and each being positioned on opposite sides of the support post 5 from one another, wherein the first 7 and second support platform 9 are substantially perpendicular in relation to the support post 5. The first 7 and second support platform 9 can, in a preferred embodiment, be horizontally adjustable so as to accommodate differing body widths of users. Again, this can be accomplished through the use of telescoping members (not shown) forming each of the first 7 and second support platform 9 members, or other configurations which would be apparent to workers skilled in the art.

Positioned upon the first 7 and second support platforms 9 are first and second breast measurement scales (15,13), the first breast measurement scale 15 being mounted upon the first support platform 7 and the second breast measurement scale 13 being mounted upon the second support platform 9, whereby the first breast measurement scale 15 measures a weight of a first breast (not shown) and the second breast measurement scale 13 measures a weight of a second breast (not shown) so as to enable a surgeon to determine a quantity of breast tissue which must be removed during the breast reduction surgery from each of the first breast and the second breast so as to substantially provide a symmetric balance in a size and shape between the first breast and the second breast after the surgery is completed. In an alternative embodiment, the first and second breast measurement scales (15,13) are also horizontally adjustable. In a still further preferred embodiment of the present invention, the first and second breast measurement scales (15,13) are digital scales, which provide an accurate digital readout of the weight of each breast.

Positioned upon the upper end of the support post 5 is a support saddle 11 for receiving and supporting a chin of a user during the measuring of the first breast and the second breast. In a preferred embodiment, the support saddle 11 is of a concave shape, as seen in FIGS. 1 and 2, so as to receive and support the chin of the user. If desired, the support saddle 11 can be padded.

Figure 3:
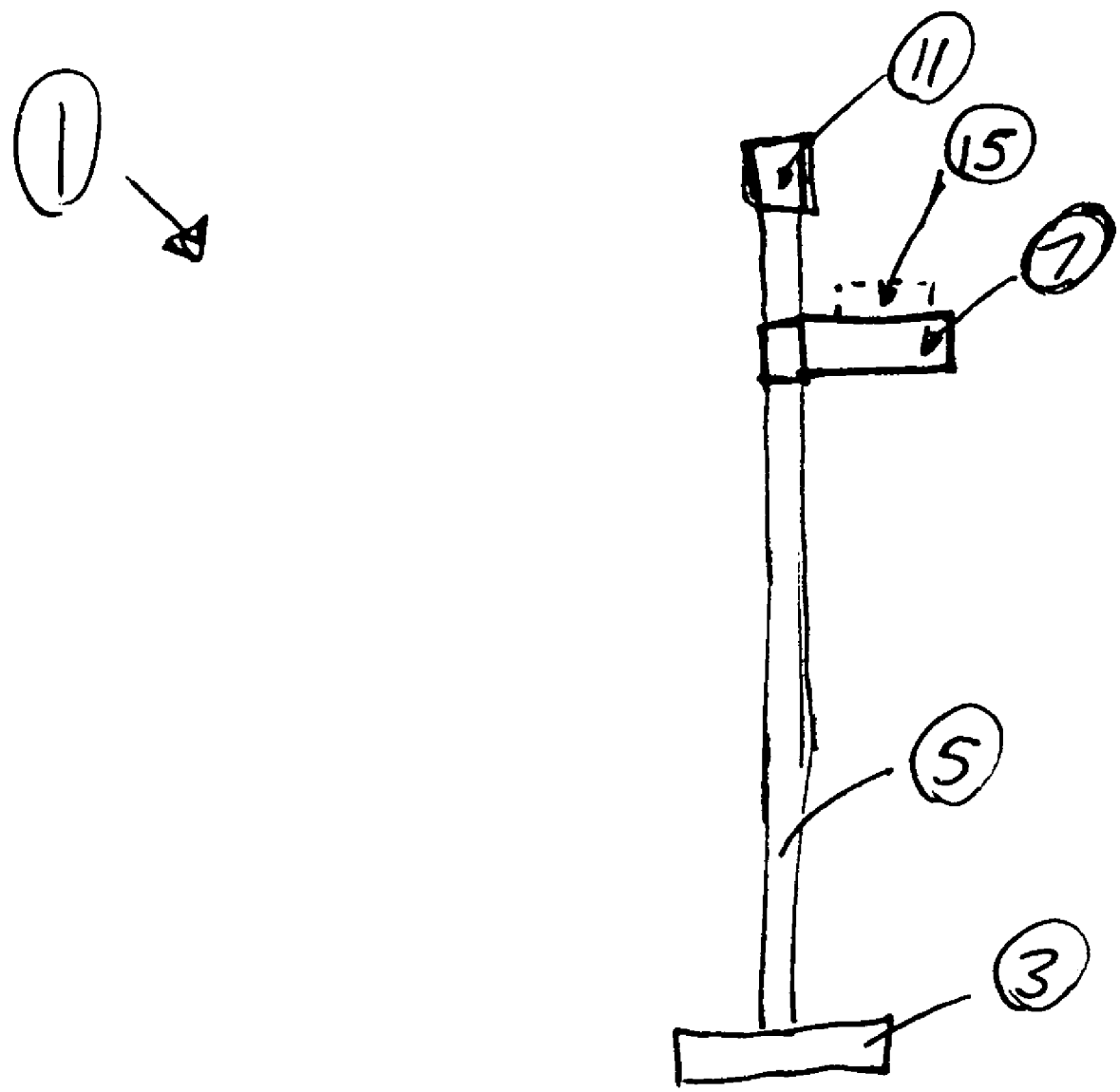
FIG. 3 is a side view of the embodiment of the breast reduction device illustrated in FIG. 1.

With respect to FIG. 3, it can be seen that the first and second breast measurement scales (15,13) extend outwardly from the support post 5, whereby, during the measuring of the first breast and the second breast (not shown), the first breast and the second breast are placed upon an upper surface of the scales on the support platform (seen as reference numeral 7 in FIG. 3), whereby the weight of the first breast and the second breast is measured.

Figure 4:
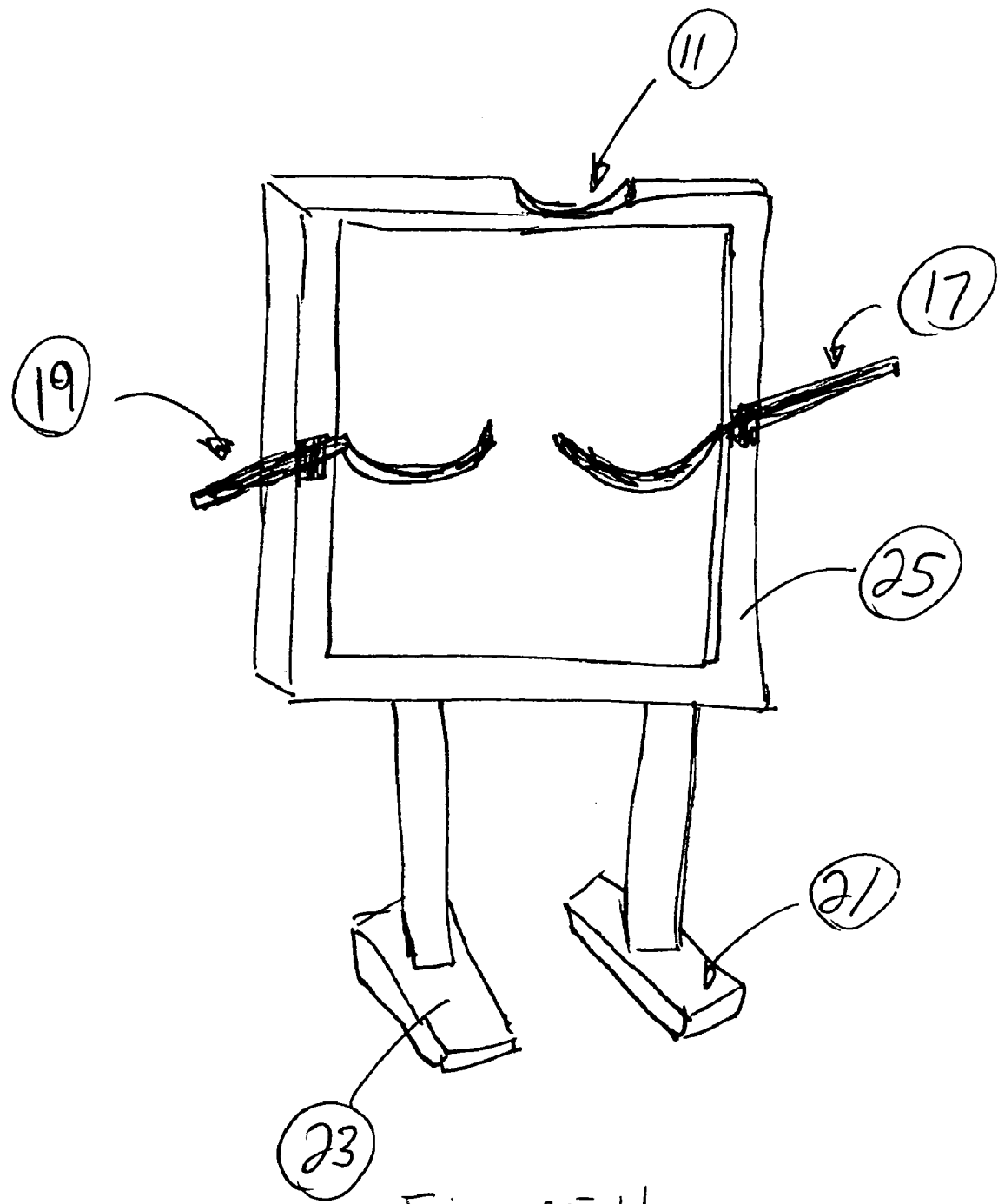
FIG. 4 illustrates another embodiment of the breast reduction device of the present invention.

FIG. 4 illustrates an alternative embodiment of the present invention, wherein the breast reduction device of the present invention comprises a square frame portion 25 mounted on two base portions (21,23). Positioned upon the upper end of the square frame portion 25 is a support saddle 11 for receiving and supporting a chin of a user during the measuring of the breasts (not shown). In a preferred embodiment, the support saddle 11 is of a concave shape. Positioned upon the square frame portion 25 are first and second breast measurement scales (17,19), each of which are concavely shaped so as to each "cup" a breast placed therein for measurement, in order to enhance the accurateness of the breast measuring process. The first breast measurement scale 17 measures a weight of a first breast (not shown) and the second breast measurement scale 19 measures a weight of a second breast (not shown). In this manner, from the measurements of the breasts, the surgeon is provided with an accurate assessment of how much breast tissue must be removed from each breast during surgery so as to achieve a substantially symmetrical balance in a final size and shape between the breasts after the surgery is completed.

Figure 5:
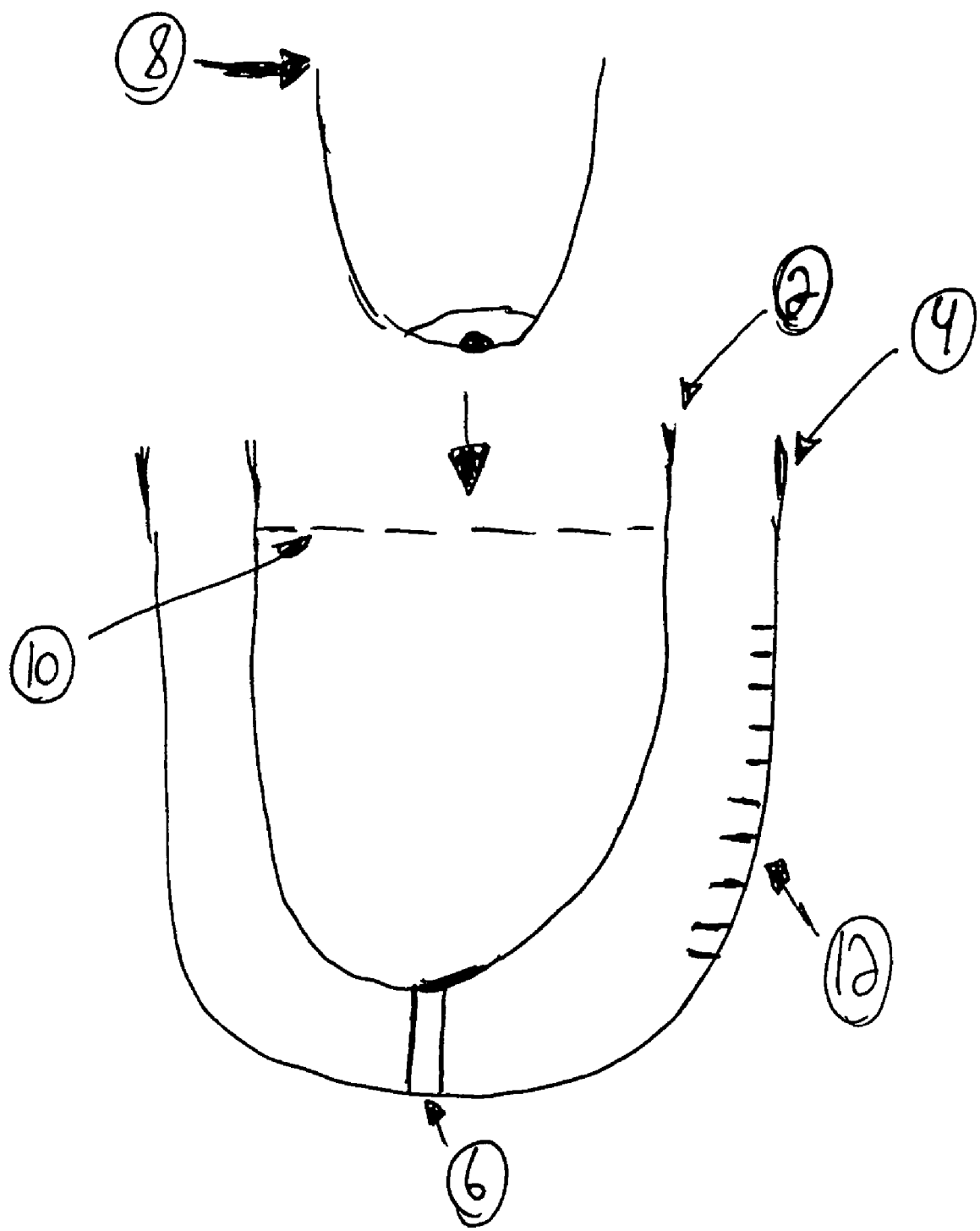
FIG. 5 illustrates another embodiment of the breast reduction device of the present invention.

FIG. 5 illustrates an alternative embodiment of the present invention, and which comprises a base portion 3 and an upstanding support post 5 mounted on the base portion 3. In one embodiment, the upstanding support post 5 can be height adjustable so as to accommodate differing body heights of users. Typically, this can be accomplished through the use of telescoping members (not shown) or other configurations which would be apparent to workers skilled in the art. At least a first support scale 77 is connected to the support post, the first support scale being positioned at a substantially upper location on the support post 5, wherein the first support scale is substantially perpendicular in relation to the support post 5. The first support scale can, in a preferred embodiment, be horizontally adjustable so as to accommodate differing body widths of users. The first support scale 77 will then have a support saddle 79 mounted thereon for receiving, and measuring, a breast of a user (In an alternative embodiment, a first and a second support scale are connected to the support post, each of the scales having a support saddle mounted thereon, for measuring each breast. Of course, during the measuring of the first breast and the second breast (not shown), the first breast and the second breast are placed upon an upper surface of the support saddles, whereby the weight of each of the breasts is measured). Further, the scales could be digital scales, which provide an accurate digital readout of the weight of each breast.

In another embodiment (not shown), the present invention could also be utilized as a breast support saddle which can be rested comfortably on the torso of a user, whereby the weight of each of the breasts is supported and measured by a support saddle mounted on support scales, and which would facilitate dimensional and symmetrical measurements. Such a configuration would entail a box-frame type construction (not shown) having a base portion, side wall portions, and a top portion comprising the support saddle mounted on the support scale. The use of such a configuration could be provided on the floor, a desk, a chair, free standing, or even mounted on a wall, as would be apparent to one skilled in the art, and could also comprise a double saddle being utilized.

The present invention has been described herein with regard to preferred embodiments. However, it will be obvious to persons skilled in the art that a number of variations and modifications can be made without departing from the scope of the invention as described herein.

I claim:

1. A breast reduction apparatus for pre-operative use in breast reduction surgery, said apparatus comprising:

a base portion;

an upstanding support post mounted on the base portion, the upstanding support post being height adjustable so as to accommodate differing body heights of users;

a first and second support platform, the first and second support platform being positioned at a substantially upper location on the support post and each being positioned on opposite sides of the support post from one another, wherein the first and second support platform are substantially perpendicular in relation to the support post and horizontally adjustable so as to accommodate differing body widths of users;

first and second breast measurement scales, the first breast measurement scale being mounted upon the first support platform and the second breast measurement scale being mounted upon the second support platform, whereby the first breast measurement scale measures a weight of a first breast and the second breast measurement scale measures a weight of a second breast so as to enable a surgeon to determine a quantity of breast tissue which must be removed during the breast reduction surgery from each of the first breast and the second breast so as to substantially provide a symmetric balance in a size and shape between the first breast and the second breast after the surgery is completed; and a support saddle for receiving and supporting a chin of a user during the measuring of the first breast and the second breast, the support saddle being mounted upon the support post.

2. The breast reduction apparatus of claim 1, wherein the first and second breast measurement scales extend outwardly from the support post, whereby, during the measuring of the first breast and the second breast, the first breast and the second breast are placed upon an upper surface of the scales, whereby the weight of the first breast and the second breast is measured.

3. The breast reduction apparatus of claim 1, wherein the first and second breast measurement scales are digital scales, and each provide a digital readout of the weight of each of the first breast and the second breast.

4. Use of the breast reduction apparatus as defined in claim 1, for pre-operative use in breast reduction surgery, whereby the weight of the first breast and the weight of the second breast is measured so as to enable a surgeon to determine a quantity of breast tissue which must be removed during the breast reduction surgery from each of the first breast and the second breast so as to substantially provide a symmetric balance in a size and shape between the first breast and the second breast after the surgery is completed.

5. A breast reduction method for pre-operative use in breast reduction surgery which utilizes the breast reduction apparatus as defined in claim 1 comprising:

utilizing the first breast measurement scale to measure a weight of a first breast;

utilizing the second breast measurement scale to measure a weight of a second breast;

determining, based upon the measurements of the weight of the first and the second breast, a quantity of breast tissue which must be removed during the breast reduction surgery from each of the first breast and the second breast so as to substantially provide a symmetric balance in a size and shape between the first breast and the second breast after the surgery is completed; and removing the determined quantity of breast tissue from each of the first breast and the second breast.

6. A breast reduction apparatus for pre-operative use in breast reduction surgery, said apparatus comprising:

a base portion;

an upstanding support post mounted on the base portion, the upstanding support post being height adjustable so as to accommodate differing body heights of users;

at least one breast measurement scale being positioned at a substantially upper location on the support post, wherein the at least one breast measurement scale is substantially perpendicular in relation to the support post and horizontally adjustable so as to accommodate differing body widths of users; and at least one support saddle, the at least one support saddle being mounted upon the at least one breast measurement scale, whereby the at least one breast measurement scale measures a weight of a breast placed thereon so as to enable a surgeon to determine a quantity of breast tissue which must be removed during the breast reduction surgery from the breast.

7. The breast reduction apparatus of claim 6, wherein the first and the second breast measurement scales are digital scales, and each provide a digital readout of the weight of each of the first breast and the second breast.

8. The breast reduction apparatus of claim 6, wherein the apparatus further comprises:

first and second breast measurement scales each being positioned at a substantially upper location on the support post and each being positioned on opposite sides of the support post from one another, wherein the first and second breast measurement scales are substantially perpendicular in relation to the support post and horizontally adjustable so as to accommodate differing body widths of users; and a first and a second support saddle, the first support saddle being mounted upon the first breast measurement scale and the second support saddle being mounted upon the second breast measurement scale, whereby the first breast measurement scale measures a weight of a first breast and the second breast measurement scale measures a weight of a second breast so as to enable a surgeon to determine a quantity of breast tissue which must be removed during the breast reduction surgery from each of the first breast and the second breast so as to substantially provide a symmetric balance in a size and shape between the first breast and the second breast after the surgery is completed.

\* \* \* \* \*